United States Patent [19]

Blanco et al.

[11] Patent Number: 5,109,850
[45] Date of Patent: May 5, 1992

[54] AUTOMATIC BLOOD MONITORING FOR MEDICATION DELIVERY METHOD AND APPARATUS

[75] Inventors: Ernesto E. Blanco, Belmont; Rosina Samadani, Cambridge, both of Mass.

[73] Assignee: Massachusetts Institute of Technology, Cambridge, Mass.

[21] Appl. No.: 746,070

[22] Filed: Aug. 12, 1991

Related U.S. Application Data

[63] Continuation of Ser. No. 477,679, Feb. 9, 1990, abandoned.

[51] Int. Cl.⁵ .............................................. A61B 5/00
[52] U.S. Cl. .................................. 128/635; 604/890.1; 604/891.1; 604/4; 604/50
[58] Field of Search .......................... 128/632, 635; 604/891.1, 890.1, 4, 50–53

[56] References Cited

U.S. PATENT DOCUMENTS

| | | |
|---|---|---|
| 3,847,138 | 11/1974 | Gollub . |
| 3,878,830 | 4/1975 | Bicher . |
| 4,403,984 | 9/1983 | Ash et al. . |
| 4,596,575 | 6/1986 | Rosenberg et al. . |
| 4,633,878 | 1/1987 | Bombardieri . |
| 4,714,462 | 12/1987 | DiDomenico . |
| 4,721,677 | 1/1988 | Clark, Jr. ............... 128/635 |
| 4,759,371 | 7/1988 | Franetzki ............... 128/632 |
| 4,805,624 | 2/1989 | Yao et al. . |
| 4,822,336 | 4/1989 | DiTraglia ............... 128/635 |
| 4,841,974 | 6/1989 | Gumbrecht et al. ..... 128/635 |
| 4,844,097 | 7/1989 | Bellhouse et al. ...... 128/635 |
| 4,854,322 | 8/1989 | Ash et al. ............... 128/635 |
| 4,974,592 | 12/1990 | Branco ................... 128/635 |
| 4,979,509 | 12/1990 | Hakky ................... 128/635 |
| 5,002,055 | 3/1991 | Merki et al. ........... 128/635 |
| 5,058,416 | 10/1991 | Engelhardt et al. .... 128/632 |

Primary Examiner—Lee S. Cohen
Assistant Examiner—K. M. Pfaffle
Attorney, Agent, or Firm—Hamilton, Brook, Smith & Reynolds

[57] ABSTRACT

An implantable blood monitoring and medication administering system includes an infusion device (2) which is implantable beneath the skin of a human or animal and which contains medication. A catheter (4) which is implantable in a vessel V is connected to the infusion device. An information transmitting sensor (22) is located in the catheter (4) and is connected to a microprocessor (8) within the system which controls a pump (10) for first withdrawing blood from the vessel V and submitting it to the sensor (22) and then returning the withdrawn blood to the vessel V along with a predetermined amount of medication, the pump may act to pump medication as well as blood or to pump blood alone. In the latter instance, a second pump (44) acts to pump the medication.

20 Claims, 3 Drawing Sheets

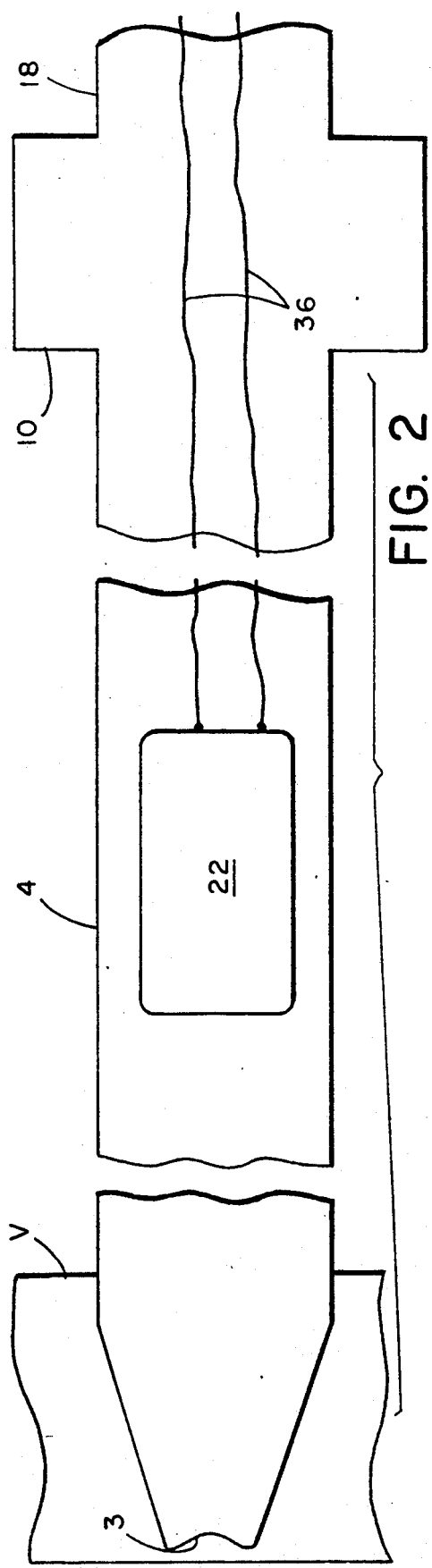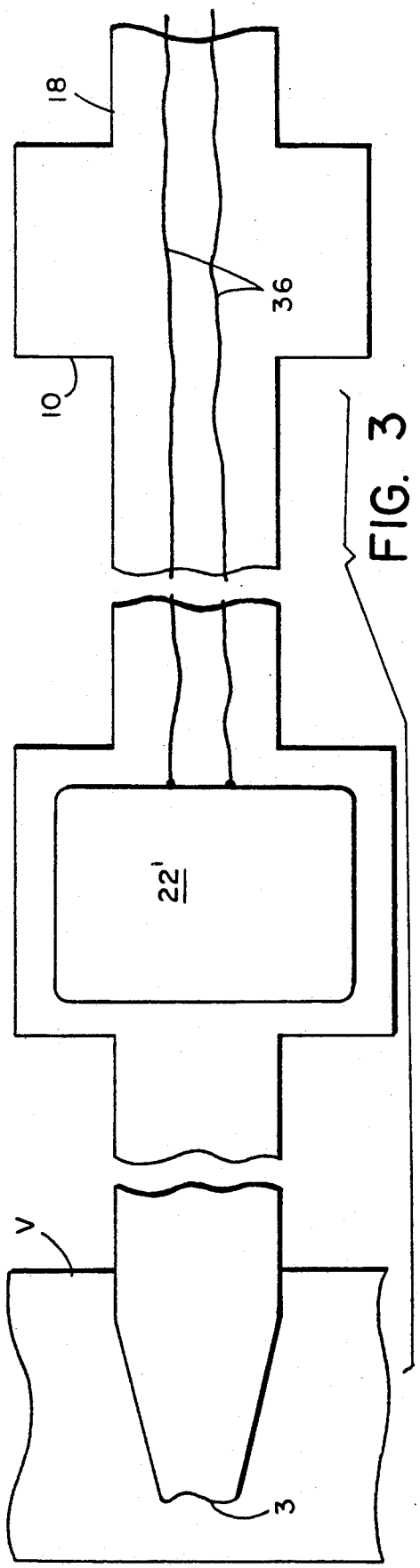

AUTOMATIC BLOOD MONITORING FOR MEDICATION DELIVERY METHOD AND APPARATUS

This is a continuation of co-pending application Ser. No. 07/477,679 filed on Feb. 9, 1990, now abandoned.

FIELD OF THE INVENTION

This invention relates to an implantable blood monitoring and medication delivery method in general and, more particularly, to an implantable blood glucose monitoring system with means for infusing insulin as determined by the glucose monitoring for the control of blood glucose levels in diabetic patients, all of which is performed by apparatus within the body.

BACKGROUND OF THE INVENTION

Among the serious metabolic diseases, the most common is diabetes mellitus, which is commonly known as diabetes and affects many millions of people around the world. The disease is characterized by a defective pancreas. The pancreas is the gland which is responsible for the secretion of insulin which controls the blood glucose level. It produces digestive enzymes which are secreted into the duodenum where they digest and neutralize food passing from the stomach to the intestine.

Diabetes mellitus or secondary diabetes stems from causes other than genetic defects, e.g., a destroyed pancreas. It results in hyperglycemia, which is excess glucose in the blood. It also results in excretable glucose in the urine and may lead to increased liver production of organic acids. The latter can result in coma and possible death. Hence, the need for continuous monitoring of blood glucose levels and the administration of insulin to control those levels.

The most widely used method to control blood glucose level is a program of single, daily injections of insulin, and many patients have been taught to do this themselves. However, commercially available implantable pumps improve upon this method by injecting insulin, upon signal, into the blood stream several times a day in smaller doses. The pump is refilled with insulin once or twice a month by injection. This reduces the number of externally administered injections the patient must undergo and also allows preprogrammed variable amounts of insulin to be released at different times into the blood stream.

The implantable pump, however, has to be activated by an externally generated signal after the patient himself has withdrawn a drop of blood, for example, from a finger, and subjected it to an analysis. This procedure is obviously somewhat painful, time consuming and, if neglected, injurious to the patient.

Implantable drug delivery systems are relatively new. The first animal implant was performed in 1971, and in a human in the middle 1970's for the delivery of heparin in the treatment of chronic thromboembolic disease. In 1980 the first insulin delivery pump was implanted in a diabetic patient. Insulin infusion devices are currently implanted in over 200 diabetic patients worldwide today. Most pumps are implanted into the subcutaneous tissue in the chest area with an infusion catheter threaded intraveneously to a central location, such as the right atrium.

There are at least two types of implantable pumps used today. One is a constant basal rate flow device in which the amount of flow is regulated by the length of the catheter used. The length and diameter of the catheter is fixed at manufacture. However, its rate of flow varies with increases in temperature and in altitude.

The second type is a programmable infusion device which delivers insulin in small, discrete doses. The output of this type of device is digitally controlled by the patient under physician supervision. A radio transmitter is used to input the correct rate, time and amount of each dose via low-frequency waves which permeate flesh. The transmitter is located outside the body but close to the location of the pump which is implanted within the body.

Implanted pumps have several advantages over the more generally used diabetic treatments, such as self-administered tests and injections. Far fewer external injections and, therefore, greater patient ease results. Also, when compared, for example, with the extreme case of replacing an organ such as the pancreas, the single greatest advantage of an implanted infusion device is that there is an ultimate limitation of organs available for transplant.

Artificial pumps can be mass produced and are far more readily available than donor organs. Pumps also have the advantage of being compatible with every blood type and, therefore, do not have to be a specific blood type as donor organs must be.

External insulin pumps, as distinguished from implantable pumps, are cumbersome and are often associated with skin irritation at the point of fusion. In comparing microprocessor control programmable electric pumps with constant rate infusion devices, the former are generally preferred because the constant rate infusion devices cannot cope with fluctuations of insulin requirements on a day-to-day or hour-to-hour basis, and perfect glycaemic control is not possible as with microprocessor controlled pumps.

Major problems, however, do exist with implantation devices. Thrombosis around the tip of the infusion catheter or slowdown or succession of the pump are serious problems that reduce insulin flow into the blood stream. A reduction of the flow of insulin has been the result of insulin aggregation or fibron deposition within the catheter, clotting of the blood in contact with the catheter, particularly at the tip, is a problem. Flushing with an alkaline solution or fibrolitic agent or a tipectomy (i.e., removal of a portion of the catheter tip) may solve the problem. Obviously, however, these remedies require surgical procedures and, occasionally, the entire catheter and/or pump must be replaced.

Present day implanted pumps are open-loop systems or one-way systems (i.e., glucose sensing and testing is external and medication infusion is unidirectional upon signal). Severe hypoglycemia (an abnormal decrease of blood sugar) due to an insulin overdose and ketoacidosis (an excess of ketones in the blood stream due to an insulin deficiency) are eminent dangers of open-loop implanted pumps. These problems, obviously, can result from human error in monitoring and/or sensing glucose level or in calculating dosage incorrectly.

Accordingly, it is one of the broader objects of the present invention to produce a blood analyzing and medication delivery method and mechanism for performing the same, which has greater patient safety and comfort.

Another object is to produce a combined blood monitoring and medication administering system which is completely implantable in a human or animal.

It is yet another object of the present invention to produce a completely automatic blood monitoring and insulin administering system which is free of human error and which does not require activation by the patient.

SUMMARY OF THE INVENTION

The invention resides in a method of automatically monitoring blood chemistry and administering medication determined to be required by the chemistry, all of which is performed within the body of a human or animal. In addition, apparatus for performing all the method steps is disclosed.

The method in its broadest form involves first withdrawing blood from a vessel in the body and then submitting the withdrawn blood to analysis within the body. From the analysis, an amount of medication is automatically calculated whereupon the blood is returned to the vessel along with the medication.

While all steps take place totally within the body of a human or animal, there is a relative spacial relationship between where the blood is withdrawn, where it is analyzed and where the quantity of medication is calculated. The following relationships exist: A signal is sent from a first location within a body to withdraw blood from a vessel. The withdrawn blood is conducted to a second location within the body for chemical analysis. Upon an analysis being made, information concerning the withdrawn blood goes from the second location (i.e., where the analysis takes place) to the first location where the initial signal came from. At the first location, the amount of medication, as required by the analysis, is computed whereupon a second signal is generated to initiate returning the withdrawn blood, as well as returning to the vessel the required amount of medication predicated upon the blood analysis.

The apparatus for carrying out the method comprises an implantable blood monitoring and medication administering system which includes an infusion device implantable beneath the skin of a human or animal and containing medication. A catheter which is implantable in a vessel is connected to the infusion device. There is an information transmitting sensor associated with the catheter which also communicates with the infusion device for delivering information concerning blood chemistry to the infusion device and there are means associated with the infusion device for causing the medication to flow through the catheter and into the vessel automatically in response to the information transmitted from the sensor. The mechanism associated with the infusion device allowing blood to flow first through the catheter from the vessel to the sensor and, subsequently, for returning the blood to the vessel with a calculated amount of medication from the infusion device, is a double-acting pump.

A microprocessor is associated with the infusion device for initiating flow of blood from the vessel to the sensor, for returning the blood to the vessel with a calculated amount of medication from the infusion device and for controlling not only a reversible pump for affecting flow in reverse directions, but in controlling valves.

The result is an implantable blood monitoring and medication administering system which is completely implantable in a human or animal, which results in greater patient safety and comfort, is free of human error, and does not require activation by the patient. There is less likelihood of blood clotting at the orifice of the catheter due to frequent "washing" by the medication flowing through the catheter or at the sensor which also is subjected to intermediate exposure to blood and, subsequently, to "washing" by the medication, as for example, insulin.

The above and other features of the invention, including various novel method steps and details of construction and combinations of parts will be more particularly described with reference to the accompanying drawings and pointed out in the claims. It will be understood that the particular automatic blood monitoring and medicating method and apparatus embodying the invention is shown by way of illustration only and not as a limitation of the invention. The principles and features of this invention may be employed and varied in numerous embodiments without departing from the scope of the invention.

BRIEF DESCRIPTIONS OF THE DRAWINGS

FIG. 2 is a schematic showing one manner of incorporating a blood sensor in the system of FIG. 1.

FIG. 3 is a schematic showing an alternate manner of incorporating a blood sensor in the system of FIG. 1.

DETAILED DESCRIPTION OF THE INVENTION

Figure 1:
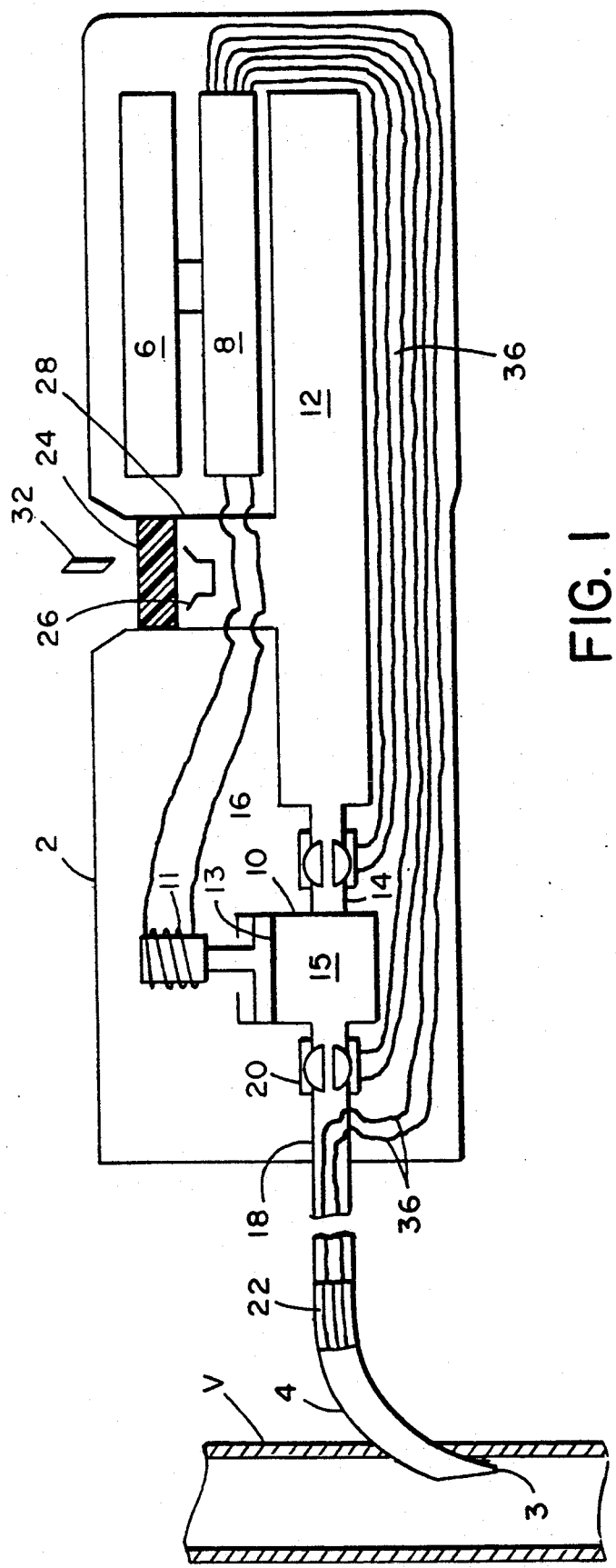
FIG. 1 is a schematic showing of an implantable blood monitoring and medication administering system.

In illustrative implantable blood monitoring and medication administrating device will be seen in FIG. 1. It includes a sealed case 2 and a catheter 4 which is implanted in a vessel V. Within the casing is a battery 6, such as a long-life lithium power cell, and a microprocessor 8. Also located in the casing is a medication infusion pump 10 herein illustrated as a solenoid operated, double acting piston pump. The pump may also be a bellows pump of a type hereinafter to be described in greater detail. A medication reservoir 12 is in communication with the pump 10 by way of a conduit 14 in which there is located a valve 16, herein illustrated schematically as an electrically operated rotary valve.

The pump 10 communicates with the catheter 4 by way of a conduit 18 which includes a second rotary valve 20. A sensor, generally indicated 22 and to be described in greater detail hereafter, is located in the catheter 4. Parenthetically, the end of the catheter 3 should be sufficiently small that if the sensor 22 should come loose, it cannot enter the blood stream. Furthermore, if the sensor disconnects, the microprocessor is preprogrammed to send an alarm so that the patient will be notified.

A glucose sensor 22 is attached in one of its two proposed configurations to the pump's insulin delivery catheter 4. The appropriate configuration is dependent on the size of sensor used. The mechanism by which blood will be sensed is the same for both configurations.

Design configurations of the sensor are shown in FIGS. 2 and 3. In the configuration shown in FIG. 2, the sensor 22 is smaller than the inner diameter of the catheter 4 and fits into the catheter. This illustrative catheter has, for example, an inner diameter of 0.6 mm and an outer diameter of 2.3 mm. The configuration shown in FIG. 3 is for larger sensors 22'. The catheter 4 is cut and a larger catheter 22' is attached, as indicated in the diagram for the length required by the sensor.

In both configurations, the sensor 22 or 22' is attached to the microprocessor via electrode leads 36. The FIG. 2 configuration has the advantage that no cuts need to be made into the existing catheter and, therefore, leaks need not be considered as a possible problem as in the configuration of FIG. 3.

An inlet septum herein illustrated as a biocompatible elastomeric plug 24 closes off the neck 28 of the medication reservoir 12. A needle stop 26 may be located in the neck 28 of the reservoir.

The case 2 is implanted in the subcutaneous tissue in the chest area and the infusion catheter 4 is threaded intravenously to a central location, such as the right atrium. The device is inserted subcutaneously with the septum 24 facing outwardly so that it may be refilled periodically by a physician. The reservoir is filled with medication, such as insulin, by a needle 32 through the inlet septum 24. Depth of penetration is limited by the needle stop 26. The septum may, for example, be made of biocompatible silicon rubber, as well as the infusion catheter.

The solenoid activator 11 of the pump 10, the sensor 22 and the valves 16 and 20 are connected by appropriate leads, designated collectively 36, to the microprocessor 8.

Operation is as follows. The microprocessor 8 is preprogrammed before implantation such that at a desired time, blood is drawn into the catheter 4 at least as far as the sensor 22 and, preferably, not much further. This is accomplished by the microprocessor 8 causing the piston 13 of the double acting pump 10 to move upwardly, with both of the valves 16 and 20 in their open positions, as shown. During the withdrawal of blood from the vessel V, the valves are maintained by the microprocessor in their open positions. At a predetermined time, before the blood reaches the pump 10 or the valve 20, the microprocessor 8 initiates closure of the valve 20 and no further blood is withdrawn, it being sufficient for the blood to reach the sensor 22, but go no further. The valve 16 remains open at this time in order to fill the pump cylinder 15 with insulin from the reservoir 12.

As soon as the blood has reached the sensor 22, it samples the blood sugar and data are sent back to the microprocessor 8. The microprocessor in turn, depending upon the information received from the sensor, calculates the amount of insulin to be injected. It than causes the valve 16 to be closed and the valve 20 to be opened. The pump 10 is then activated with the piston 13 moving downwardly. This forces the insulin out through the valve 20, causing the blood then in the catheter to return to the vessel followed by a measured, calculated dose of insulin.

In this process, the sensor 22 is "washed" by the flowing insulin as is the orifice 3 of the catheter.

The above described mechanism is illustrative of one type of apparatus for carrying out the invention. It will be obvious that its construction, and the use of other components and existing devices may be modified or substituted in the system.

Figure 4:
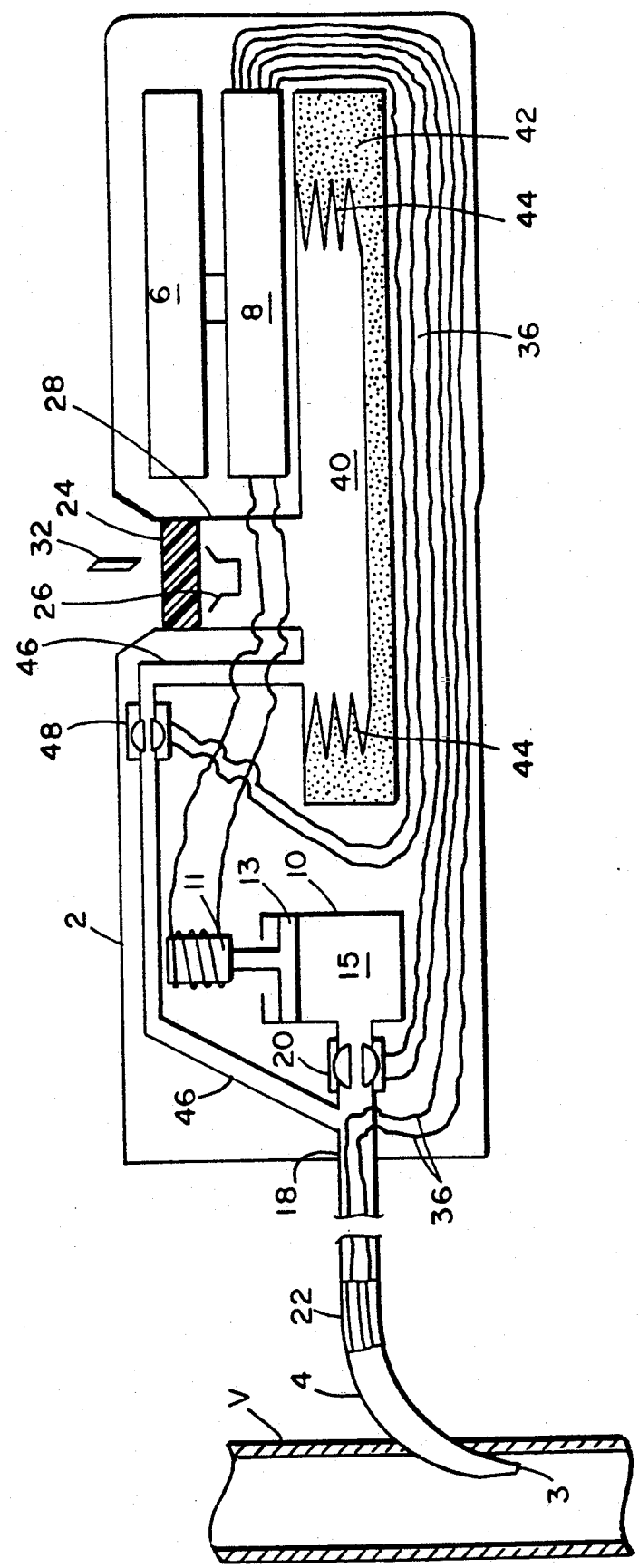
FIG. 4 is a schematic showing of an implantable blood monitoring and medication system similar to that shown in FIG. 1, but having a different embodiment of the pumping system.

Referring to FIG. 4, there will be seen an alternative embodiment of the pumping system. It employs a constant basal-flow rate pump of the type manufactured by Infusaid of Norwood, Mass. The pump consists of a drug chamber, a reservoir 40 and a power supply chamber 42. Titanium bellows 44 separate the two chambers and act as a spring acting on the drug chamber 40. The power supply chamber 42 contains fluid which boils at body temperature and, therefore, exists in equilibrium with its vapor and exerts a constant pressure on the drug chamber 40.

Upon signal from the microprocessor, the medication is forced from chamber 40 through a passageway 46 when a valve 48 is in the open position under the control of the microprocessor 8.

With this configuration, the pump 10 has only one function and that is to draw the blood to the sensor 22 and then to return it to the vessel V.

In operation, with the valve 20 open and the valve 48 closed, the pump 15 draws the blood to the sensor 22. A signal is sent to the microprocessor 8 and the new flow rate from the bellows pump reservoir 40 would be adjusted to the level required for proper biological function. The new flow level would then continue after the blood had been returned to the vessel from the sensor area 22 until the next cycle of testing takes place. Adjustment in flow may be controlled by selecting the valve 48 as a flow-rate control valve. The other function of the valve 48 is to prevent blood from going to the reservoir 40 upon being withdrawn from the vessel V. This is a safety measure since it is only intended that the blood be drawn as far as the sensor 22.

One type of commercially available sensor which may be employed is an enzyme electrode sensor. Whereas this type sensor was developed for analytic purposes and not for closed loop systems, it is intended for use with whole blood and, therefore, ideal for use with a catheter placed directly in the blood stream.

Sensors for use with the system should, preferably, be independent of ambient temperature and have relatively short response times. The configuration as seen in FIG. 3, is the better designed option suited to sensors available in the present state of technology. This is true in spite of the fact that the catheter has to be cut and resealed so that it does not leak, but it is more easily assembled.

We claim:

1. An implantable blood monitoring and medication administering system, comprising,
    an infusion device implantable beneath the skin of a human or animal and containing medication,
    a single channel catheter implantable in a vessel and connected to the infusion device,
    an information transmitting sensor located within the single channel catheter and communicating with the infusion device for transmitting information about blood chemistry to the infusion device, and
    wherein said infusion device comprises means for causing medication to flow through the catheter, into engagement with the sensor, and thence into the vessel automatically in response to the information transmitted from the sensor.

2. An implantable blood monitoring and medication administering system according to claim 1, including a microprocessor and wherein the means for causing medication to flow through the catheter into the vessel is a pump operatively connected to and controlled by the microprocessor.

3. An implantable blood monitoring and medication administering system according to claim 1, including a microprocessor and wherein the means for causing medication to flow through the catheter into the vessel, is a bellows pump operatively connected to and controlled by the microprocessor.

4. An implantable blood monitoring and medication administering system, comprising,
   an infusion device implantable beneath the skin of a human or animal and containing medication,
   a single channel catheter implantable in a vessel and connected to the infusion device,
   medication calculating means in the infusion device;
   an information transmitting sensor located within the single channel catheter and communicating with the infusion device for transmitting information about blood chemistry to the medication calculating means, and
   wherein said infusion device comprises means for drawing blood into the catheter from the vessel to engage the sensor in the catheter and, subsequently reversing the blood flow for returning the blood along the same path through the catheter to the vessel with a calculated amount of medication from the infusion device.

5. An implantable blood monitoring and medication administering system according to claim 4, including a microprocessor and wherein the mechanism for causing medication to flow through the catheter into the vessel is a pump operatively connected to and controlled by the microprocessor.

6. An implantable blood monitoring and medication administering system according to claim 4, including a microprocessor and wherein the mechanism for allowing blood to flow through the catheter from the vessel to the sensor and for returning this blood to the vessel is a reversible pump operatively connected to and controlled by the microprocessor.

7. An implantable blood monitoring and medication administering system according to claim 4, including a microprocessor and wherein the mechanism for causing medication to flow through the catheter into the vessel, is a bellows pump operatively connected to and controlled by the microprocessor.

8. An implantable blood monitoring and medication administering system according to claim 4, wherein said means for drawing blood into the catheter and for causing the blood to flow to the sensor and to return to the vessel is a pump.

9. An implantable blood monitoring and medication administering system according to claim 4, wherein said mechanism for drawing blood into the catheter is a pump operatively connected to the catheter for causing the blood to flow to the sensor and for returning the blood to the vessel and further comprising a second pump to cause medication to flow from the infusion device to the vessel.

10. An implantable blood monitoring and medication administering system according to claim 4, wherein said mechanism for drawing blood is a reversible pump operatively connected to the catheter for causing the drawn blood to flow to the sensor and for returning it to the vessel.

11. An implantable blood monitoring and medication administering system, comprising,
   an infusion device implantable beneath the skin of a human or animal and containing medication,
   a single channel catheter implantable in a vessel and connected to the infusion device,
   an information transmitting sensor located within the single channel catheter and communicating with the infusion device for transmitting information about blood chemistry to the infusion device, and
   wherein said infusion device comprises a microprocessor and a pump for drawing blood from the vessel onto the catheter to engage the sensor and for returning the blood along the same path through the catheter to the vessel with a calculated amount of medication from the infusion device.

12. An implantable blood monitoring and medication administering system according to claim 11, wherein a pump is operatively connected to the catheter for causing the blood to flow to the sensor and to return to the vessel.

13. An implantable blood monitoring and medication administering system according to claim 11, wherein a second pump causes medication to flow from the infusion device to the vessel along the same path through the catheter.

14. An implantable blood monitoring and medication administering system according to claim 11, wherein the pump is reversible and is operatively connected to the catheter for drawing blood along the same path to the sensor and for returning it to the vessel along the same path.

15. A method of automatically monitoring blood chemistry and administering an amount of medication determined to be required by the chemistry monitoring, all from within the body of a human or animal, comprising the steps of:
   a) withdrawing blood from a vessel in the body;
   b) submitting the withdrawn blood to analysis within the body;
   c) determining the amount of medication required as a result of the analysis;
   d) adding the required amount of medication to the withdrawn blood; and
   e) returning the analyzed blood to the vessel along with the determined amount of medication.

16. Method according to claim 15, wherein the step of submitting the withdrawn blood to analysis occurs at a specific location different from the site of withdrawal.

17. Method according to claim 15, wherein the step of submitting the withdrawn blood to analysis occurs at a specific location different from the site of withdrawal and wherein the medication upon going to the vessel passes the specific location where the analysis took place.

18. A method of automatically monitoring blood chemistry and administering an amount of medication determined to be required by the chemistry monitoring, all from within the body of a human or animal, comprising the steps of:
   a) sending a signal from a first location within the body to withdraw blood from a vessel,
   b) transmitting the withdrawn blood to a second location within the body for chemical analysis,
   c) chemically analyzing the withdrawn blood,
   d) transmitting information about the analyzed blood from the second location to the first location,
   e) calculating at the first location within the body the amount of medication required as a result of the analysis,
   f) adding the required amount of medication to the withdrawn blood, and
   g) creating a signal at the first location to initiated returning the withdrawn blood and the required medication to the vessel.

19. Method according to claim 18, wherein the medication, upon going to the vessel, passes the second location where the analysis took place.

20. A method of automatically monitoring blood chemistry and administering an amount of medication determined to be required by the chemistry monitoring, all from within the body of a human or animal, comprising the steps of:
   a) sending a signal from a first location within the body to withdraw blood from a vessel,
   b) transferring the blood from the vessel to a second location within the body for chemical analysis of the blood,
   c) chemically analyzing the withdrawn blood at the second location,
   d) sending information about the analysis to the first location within the body and at that location calculating the amount of medication required as a result of the analysis, and
   e) creating a signal at the first location to dispense the required medication from the first location to the second location and then into the vessel along with the analyzed blood.

* * * * *